(12) United States Patent
Krebs

(10) Patent No.: US 6,875,172 B2
(45) Date of Patent: Apr. 5, 2005

(54) SURGICAL RETRACTOR SYSTEM

(75) Inventor: Robert D. Krebs, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 0 days.

(21) Appl. No.: 10/429,530

(22) Filed: May 5, 2003

(65) Prior Publication Data

US 2004/0225193 A1 Nov. 11, 2004

(51) Int. Cl.$^7$ .............................................. A61B 17/02
(52) U.S. Cl. ..................................... 600/206; 600/201
(58) Field of Search ............................. 600/201, 206, 600/207, 210, 213, 215, 214, 217, 219, 224, 227, 229, 230, 237, 238; D24/135; 2/DIG. 9, 44, 134, 463, 464; 450/141, 142, 136, 137, 116, 117

(56) References Cited

U.S. PATENT DOCUMENTS

| | | | | |
|---|---|---|---|---|
| 257,215 A | * | 5/1882 | Doyle | 600/242 |
| 744,204 A | * | 11/1903 | Jordan | 600/242 |
| 1,904,532 A | * | 4/1933 | Reiss | 281/34 |
| 1,928,943 A | * | 10/1933 | McKay | 5/484 |
| 2,450,247 A | * | 9/1948 | Moore | 27/21.1 |
| 2,614,630 A | * | 10/1952 | Moszelt | 160/370.21 |
| 2,873,544 A | * | 2/1959 | Boman | 38/140 |
| 3,139,883 A | * | 7/1964 | Collins | 602/33 |
| 3,159,854 A | * | 12/1964 | Covacevich | 441/125 |
| 3,186,089 A | * | 6/1965 | Asher | 433/5 |
| 3,286,694 A | * | 11/1966 | Landy | 119/755 |
| 3,336,969 A | * | 8/1967 | Marchman | 160/370.21 |
| 3,426,367 A | * | 2/1969 | Bradford | 5/626 |
| 3,458,935 A | * | 8/1969 | Johnson et al. | 433/5 |
| 3,490,449 A | * | 1/1970 | Ewehvahn | 450/155 |
| 3,494,658 A | * | 2/1970 | Maes, Jr. | 296/100.15 |
| 3,608,158 A | * | 9/1971 | Bengtsson | 24/170 |
| 3,916,879 A | * | 11/1975 | Cotten | 600/242 |
| 4,906,503 A | * | 3/1990 | De La Cruz et al. | 428/81 |
| 5,168,605 A | * | 12/1992 | Bartlett | 24/519 |
| 5,469,583 A | * | 11/1995 | Akeley et al. | 2/421 |
| 5,709,220 A | * | 1/1998 | Kellan | 128/849 |
| 5,800,346 A | * | 9/1998 | Adams | 600/227 |
| 5,897,087 A | * | 4/1999 | Farley | 248/229.21 |
| 5,964,698 A | * | 10/1999 | Fowler | 600/217 |
| 6,055,988 A | * | 5/2000 | Perisho | 128/869 |
| 6,190,312 B1 | * | 2/2001 | Fowler, Jr. | 600/231 |
| 6,386,588 B1 | * | 5/2002 | Young et al. | 280/821 |
| 6,616,604 B1 | * | 9/2003 | Bass et al. | 600/206 |
| 2003/0226846 A1 | * | 12/2003 | Horwath | 220/287 |

OTHER PUBLICATIONS

Thompson Surgical Instruments, Inc., Dec. 6, 2002 (2 pages) http://www.thompsonsurgical.com/cgi.

* cited by examiner

*Primary Examiner*—Eduardo C. Robert
*Assistant Examiner*—David Comstock
(74) *Attorney, Agent, or Firm*—Johnathan D. Feuchtwang; Zimmer Technology, Inc.

(57) ABSTRACT

An apparatus includes a substantially pliable sheet-like member, a surgical retractor, and a substantially elastic coupling extending between the sheet-like member and the retractor. A method for expanding a surgical cavity in a patient includes positioning the patient on a substantially pliable sheet-like member, positioning a surgical retractor in the cavity, extending a substantially elastic coupling between the sheet-like member and the retractor, and tensioning the coupling.

10 Claims, 5 Drawing Sheets

SURGICAL RETRACTOR SYSTEM

FIELD OF THE INVENTION

The present invention relates generally to the field of medicine, and, more particularly, to surgical retractor systems.

BACKGROUND

In general, surgical retractors are used to push, pull, hold and/or fold skin, flesh and/or other tissue away from a site where a surgical operation or other intervention is being performed. Retractors have been used to facilitate separation of various tissues from architectures proximal to surgical sites, thereby improving access to and visibility of the sites. Also, retractors have been used to expand cavities or working areas around such sites, providing more room in which to maneuver operating and diagnostic tools.

For cavity expansions, surgical retractors have historically been held in place either by hand or (when hands have been impractical) by rigid support frames. FIG. 1 (prior art) shows a typical retractor support frame 10. The typical retractor support frame 10 includes numerous pieces that form a scaffold-like structure around the surgical site 20. The scaffolding may be anchored to a relatively stationary structure such as the railing 30 of the surgical table on which the patient 40 lies. Various retractors (50, 60, 70, 80, 90) are secured to the frame at suitable points around the site. The typical support frame 10 may also include weight systems or other mechanisms (not shown) for tensioning the retractors in order to sufficiently enlarge the cavity.

However, the complexities of historical retractor systems are not necessary for all surgical procedures.

SUMMARY OF THE INVENTION

The present invention provides an apparatus including a substantially pliable sheet-like member, a surgical retractor, and a substantially elastic coupling extending between the sheet-like member and the retractor.

In an alternative embodiment, the present invention provides a method for expanding a surgical cavity in a patient. The method includes positioning the patient on a substantially pliable sheet-like member, positioning a surgical retractor in the cavity, extending a substantially elastic coupling between the sheet-like member and the retractor, and tensioning the coupling.

The above-noted features and advantages of the present invention, as well as additional features and advantages, will be readily apparent to those skilled in the art upon reference to the following detailed description and the accompanying drawings.

DETAILED DESCRIPTION OF EXEMPLARY EMBODIMENT(S)

Figure 1:
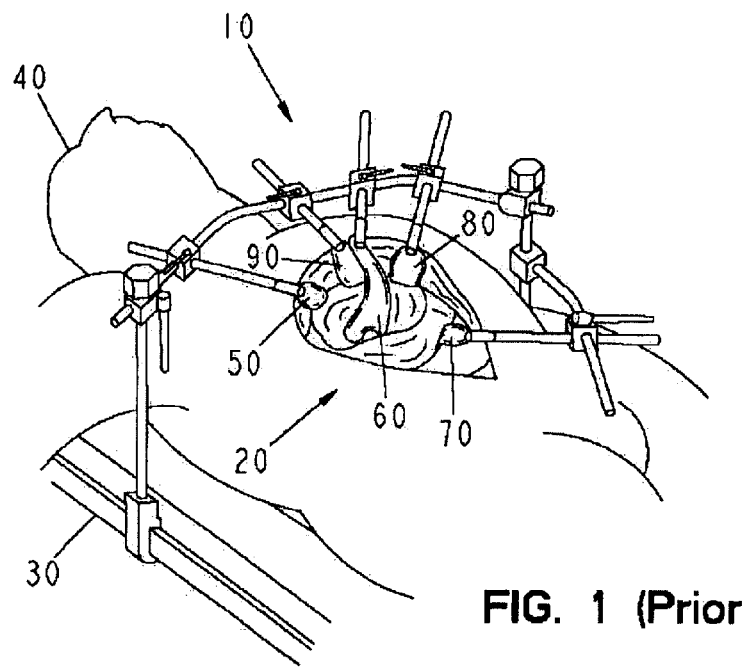
Figure 2:
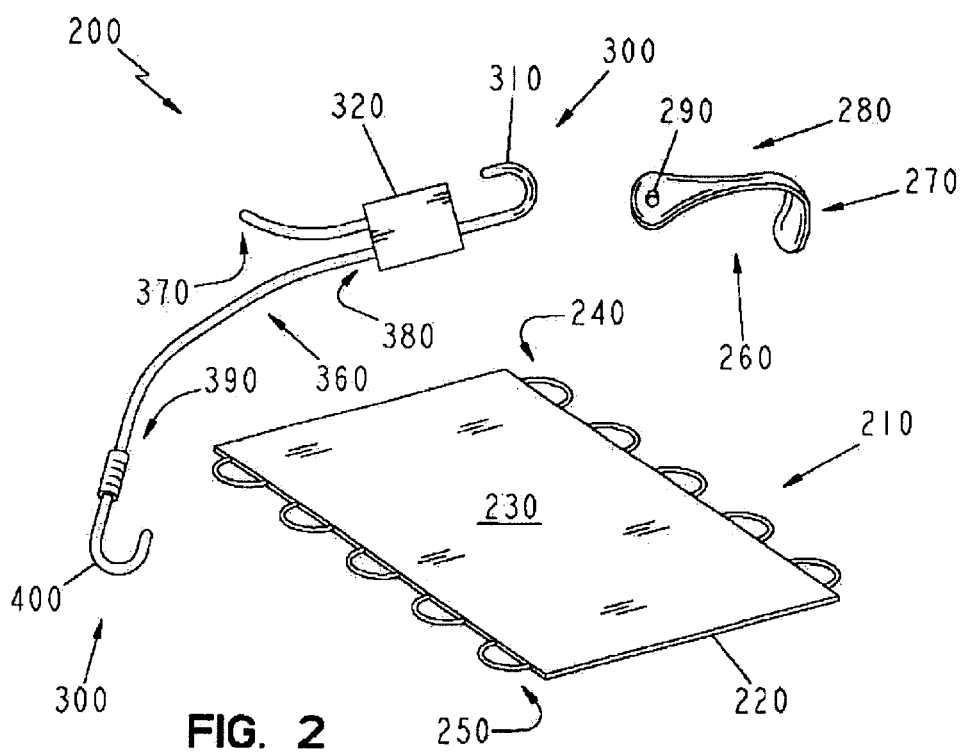
FIG. 2 shows an exploded perspective view of an exemplary surgical retractor system according to the present invention.

FIG. 2 shows an exploded perspective view of an exemplary surgical retractor system 200 according to the present invention. System 200 includes a sheet-like member 210. Member 210 includes a foundation or base 220 which forms a pliable mat, tarp, blanket, carpet, or the like upon which a patient may be situated during a surgical procedure. When flattened, base 220 has a generally rectangular upper surface 230. In exemplary system 200, member 210 is machine-washable and reusable, and base 220 is liquid-absorbent. Accordingly, in system 200 base 220 is composed primarily of cloth. However, in alternative embodiments member 210 may be washable/reusable or disposable, and/or base 220 may be liquid-absorbent, liquid-repellent, or liquid-permeable. Accordingly, in alternative embodiments base 220 may be composed primarily of cloth, plastic, rubber, or any other suitable material(s). Member 210 further includes a row of loops 240 and a row of loops 250. Each of the loops 240 is secured and arcs outwardly along one perimeter side of the base 220, and each of the loops 250 is secured and arcs outwardly along an opposing perimeter side of the base 220. In exemplary system 200, loops 240 and loops 250 are rigid and, accordingly, are composed of stainless steel. In alternative embodiments, loops 240 and loops 250 may be rigid, flexible, or pliable and, accordingly, composed of stainless steel, plastic, rubber, cloth, or any other suitable material(s).

Exemplary system 200 also includes a surgical retractor 260. In general, retractor 260 is configured in any of various known manners to pull and hold flesh and/or other tissue away from a surgical site. Accordingly, in system 200 retractor 260 includes a broad, somewhat curled blade portion 270 and a generally planar body portion 280 that extends from portion 270. Distal from portion 270, portion 280 defines a hole or aperture 290. In exemplary system 200, retractor 260 is autoclavable and reusable and, accordingly, is composed of stainless steel. In alternative embodiments, retractor 260 may be autoclavable or otherwise cleanable and reusable or it may be disposable and, accordingly, it may be composed of plastic or any other suitable material(s).

Exemplary system 200 further includes a coupling 300. In general, coupling 300 is configured to elastically couple retractor 260 to sheet-like member 210. Accordingly, in system 200 coupling 300 includes a fastener 310 engaged with retractor 260 via aperture 290. In system 200, fastener 310 is composed of a simple hook. However, in alternative embodiments fastener 310 may be composed of a post, button, screw, or any other suitable device(s). Coupling 300 further includes a catch 320. Catch 320 defines a channel 330 having a U-shaped cross section, an opening 340, and an opening 350 (see FIG. 4). Fastener 310 extends away from retractor 260 into connection with catch 320. Coupling 300 also includes an elastic strap or band 360. Band 360 includes an end portion 370, an interspatial portion 380 that extends through channel 330 such that the position of catch 320 along band 360 is fixed by friction between channel 330 and band 360 when band 360 is tensed and such that catch 320 is hand movable along band 360 when band 360 is relaxed, and an opposite end portion 390. In system 200, band 360 is composed of rubber. In alternative embodiments, band 360 may be made from any other suitable component(s). Coupling 300 further includes a fastener 400 connected to end portion 390. Fastener 400 extends away from end portion 390 into engagement with one of loops 250. In system 200, fastener 400 is composed of a simple hook that is slipped onto or around one of loops 250. However, in alternative embodiments fastener 400 may be composed of a pincer (see FIG. 7) or any other device(s) suitable for coupling end portion 390 to one of loops 250 or directly to base 220.

Figure 3:
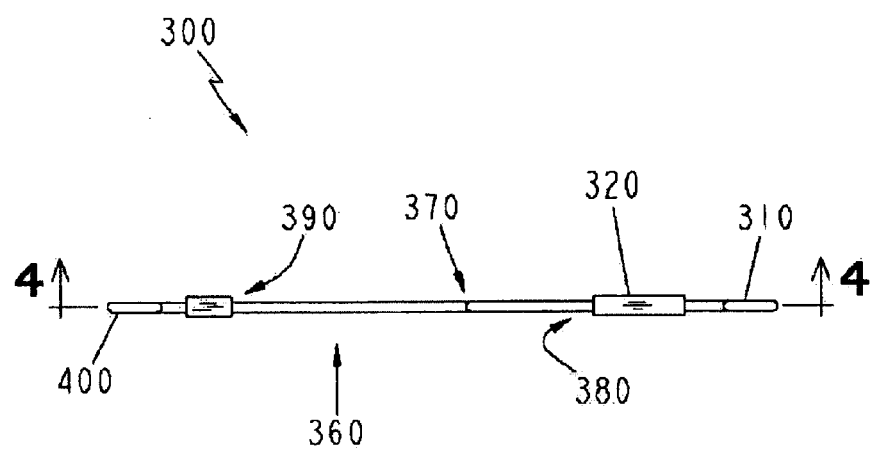
FIG. 3 shows a side view of the coupling of FIG. 2.

FIG. 3 shows a side view of coupling 300. Fastener 310, catch 320, band 360 (including end portion 370, interspatial portion 380, and opposite end portion 390), and fastener 400 are discernable in FIG. 3.

Figure 4:
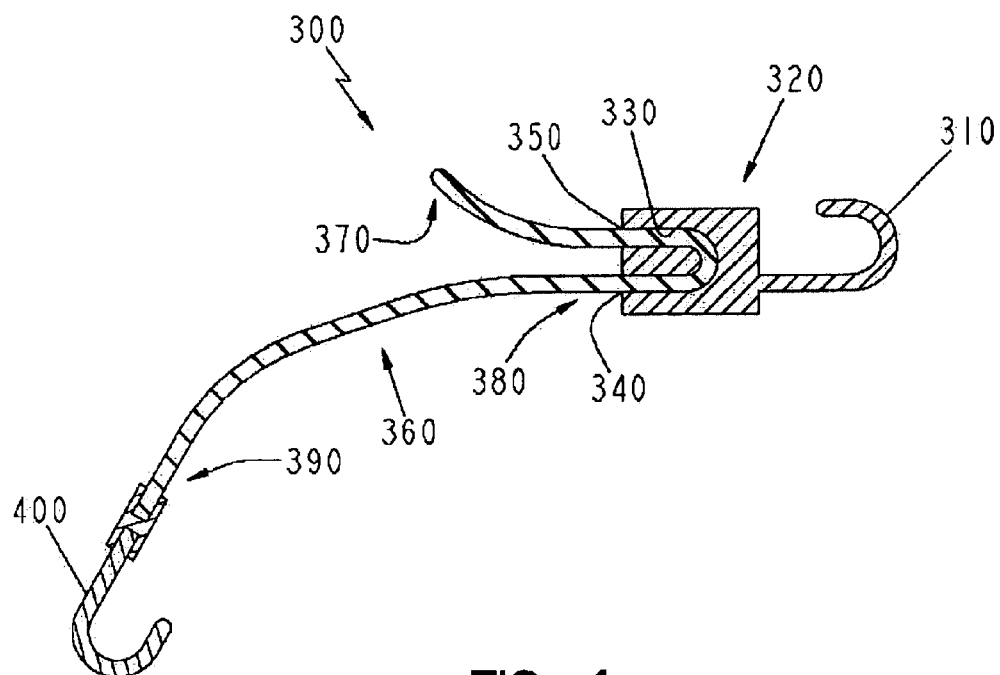
FIG. 4 shows a cross-sectional view of the coupling of FIG. 2 (and FIG. 3) along line 4—4 of FIG. 3.

FIG. 4 shows a cross-sectional view of coupling 300 along line 4—4 of FIG. 3. Fastener 310, catch 320 (including channel 330, opening 340, and opening 350), band 360 (including end portion 370, interspatial portion 380, and opposite end portion 390), and fastener 400 are discernable in FIG. 4.

Figure 5:
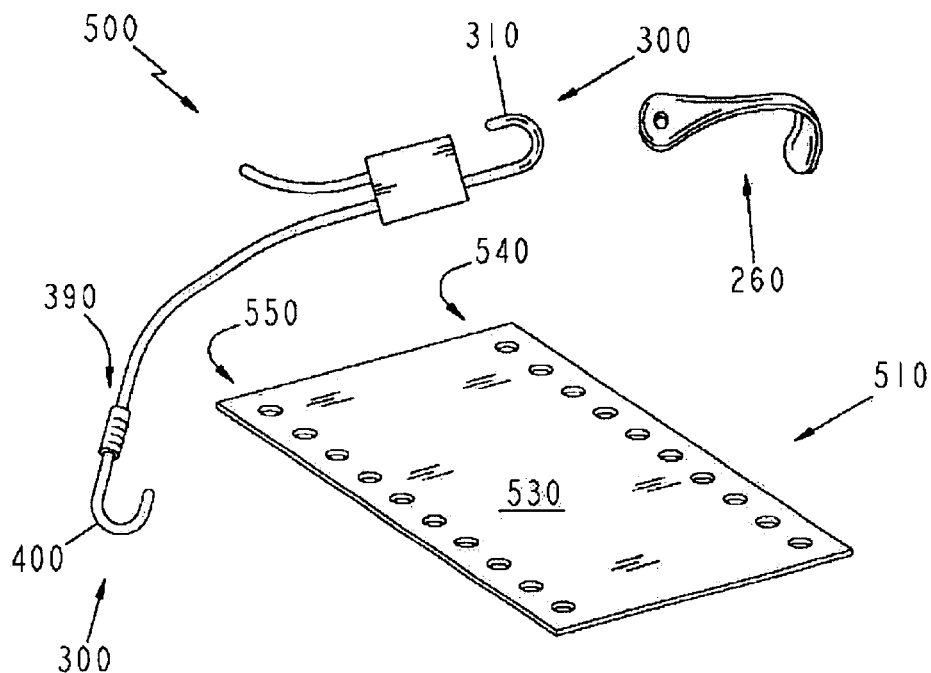
FIG. 5 shows an exploded perspective view of an exemplary alternative surgical retractor system according to the present invention.

FIG. 5 shows an exploded perspective view of an exemplary alternative surgical retractor system 500 according to the present invention. System 500 includes retractor 260 and coupling 300 (discussed above in connection with system 200). However, exemplary system 500 differs from exemplary system 200 in that system 500 includes an alternative sheet-like member 510 (in contrast to sheet-like member 210 of system 200). Like member 210, member 510 forms a pliable mat, tarp, blanket, carpet, or the like upon which a patient may be situated during a surgical procedure. When flattened, member 510 also has a generally rectangular upper surface 530. In exemplary system 500, member 510 is machine-washable, reusable, and liquid-absorbent. Accordingly, in system 500 member 510 is composed primarily of cloth. In alternative embodiments, member 510 may be washable/reusable, disposable, and/or liquid-absorbent, liquid-repellent, or liquid-permeable. Accordingly, in alternative embodiments member 510 may be composed primarily of cloth, plastic, rubber, or any other suitable material(s). However, in contrast to loops 240 and loops 250 (of member 210), member 510 defines a row of holes or apertures 540 along one perimeter side and a row of holes or apertures 550 along an opposing perimeter side. Fastener 310 engages with retractor 260 as discussed above in connection with system 200. However, in system 500 fastener 400 couples end portion 390 directly to member 510 by extending through one of apertures 550 (in contrast to its engagement with one of loops 250 in system 200).

Figure 6:
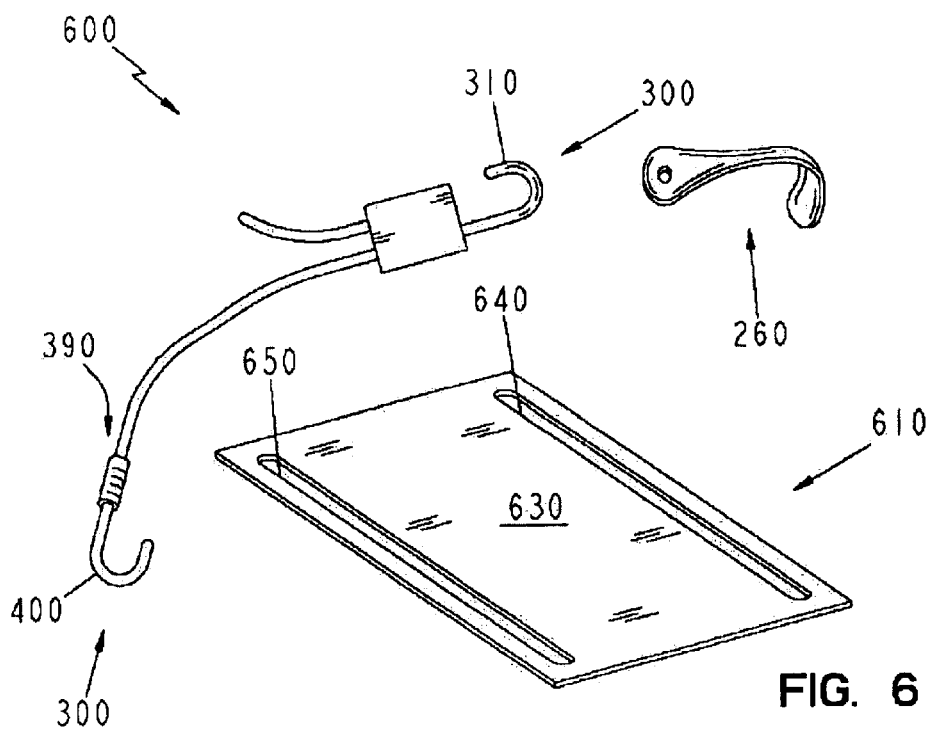
FIG. 6 shows an exploded perspective view of another exemplary alternative surgical retractor system according to the present invention.

FIG. 6 shows an exploded perspective view of an exemplary alternative surgical retractor system 600 according to the present invention. System 600 includes retractor 260 and coupling 300 (discussed above in connection with system 200). However, exemplary system 600 differs from exemplary system 200 in that system 600 includes an alternative sheet-like member 610 (in contrast to sheet-like member 210 of system 200). Like member 210, member 610 forms a pliable mat, tarp, blanket, carpet, or the like upon which a patient may be situated during a surgical procedure. When flattened, member 610 also has a generally rectangular upper surface 630. In exemplary system 600, member 610 is machine-washable, reusable, and liquid-absorbent. Accordingly, in system 600 member 610 is composed primarily of cloth. In alternative embodiments, member 610 may be washable/reusable, disposable, and/or liquid-absorbent, liquid-repellent, or liquid-permeable. Accordingly, in alternative embodiments member 610 may be composed primarily of cloth, plastic, rubber, or any other suitable material(s). However, in contrast to loops 240 and loops 250 (of member 210), member 610 defines an oblong hole or aperture 640 along one perimeter side and an oblong hole or aperture 650 along an opposing perimeter side. Fastener 310 engages with retractor 260 as discussed above in connection with system 200. However, in system 600 fastener 400 couples end portion 390 directly to member 610 by extending through apertures 650 (in contrast to its engagement with one of loops 250 in system 200).

Figure 7:
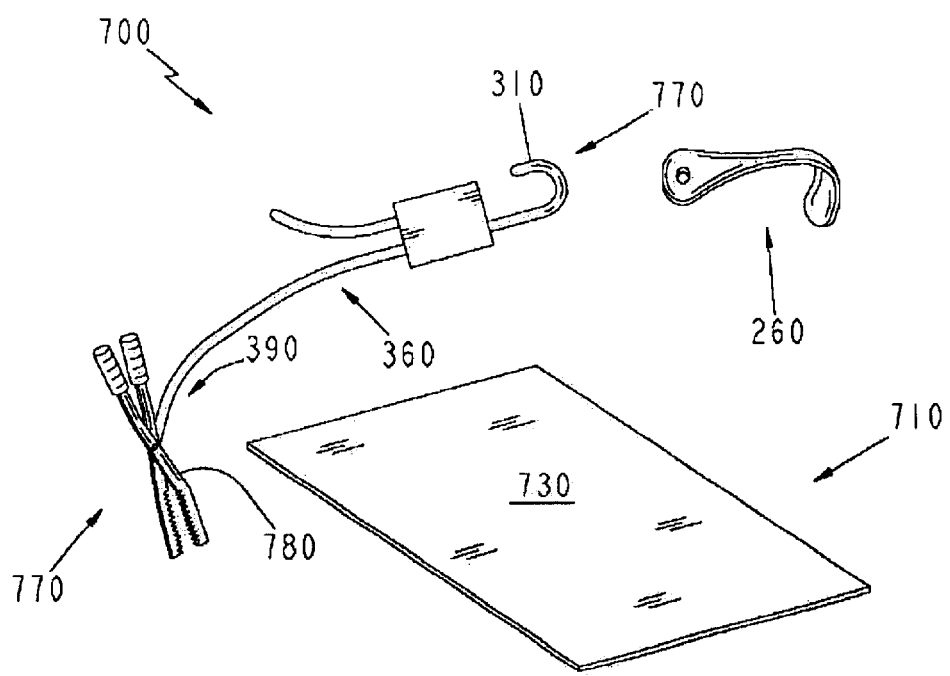
FIG. 7 shows an exploded perspective view of yet another exemplary alternative surgical retractor system according to the present invention.

FIG. 7 shows an exploded perspective view of an exemplary alternative surgical retractor system 700 according to the present invention. System 700 includes retractor 260 (discussed above in connection with system 200). However, exemplary system 700 differs from exemplary system 200 in that system 700 includes an alternative sheet-like member 710 (in contrast to sheet-like member 210 of system 200) and an alternative coupling 770 (in contrast to coupling 300). Like member 210, member 710 forms a pliable mat, tarp, blanket, carpet, or the like upon which a patient may be situated during a surgical procedure. When flattened, member 710 also has a generally rectangular upper surface 730. In exemplary system 700, member 710 is machine-washable, reusable, and liquid-absorbent. Accordingly, in system 700 member 710 is composed primarily of cloth. In alternative embodiments, member 710 may be washable/reusable, disposable, and/or liquid-absorbent, liquid-repellent, or liquid-permeable. Accordingly, in alternative embodiments member 710 may be composed primarily of cloth, plastic, rubber, or any other suitable material(s). However, in contrast to member 210 (FIG. 2), member 510 is (FIG. 5), and member 610 (FIG. 6), member 710 includes no loops and defines no apertures, respectively. Coupling 770 is configured in a like manner to coupling 300 except that coupling 770 includes a spring-loaded pincer 780 that couples end portion 390 (of band 360) directly to one perimeter side of member 710 (in contrast to the engagement of the hooked embodiment of fastener 400 with one of loops 250 in system 200). Fastener 310 engages with retractor 260 as discussed above in connection with system 200.

Figure 8:
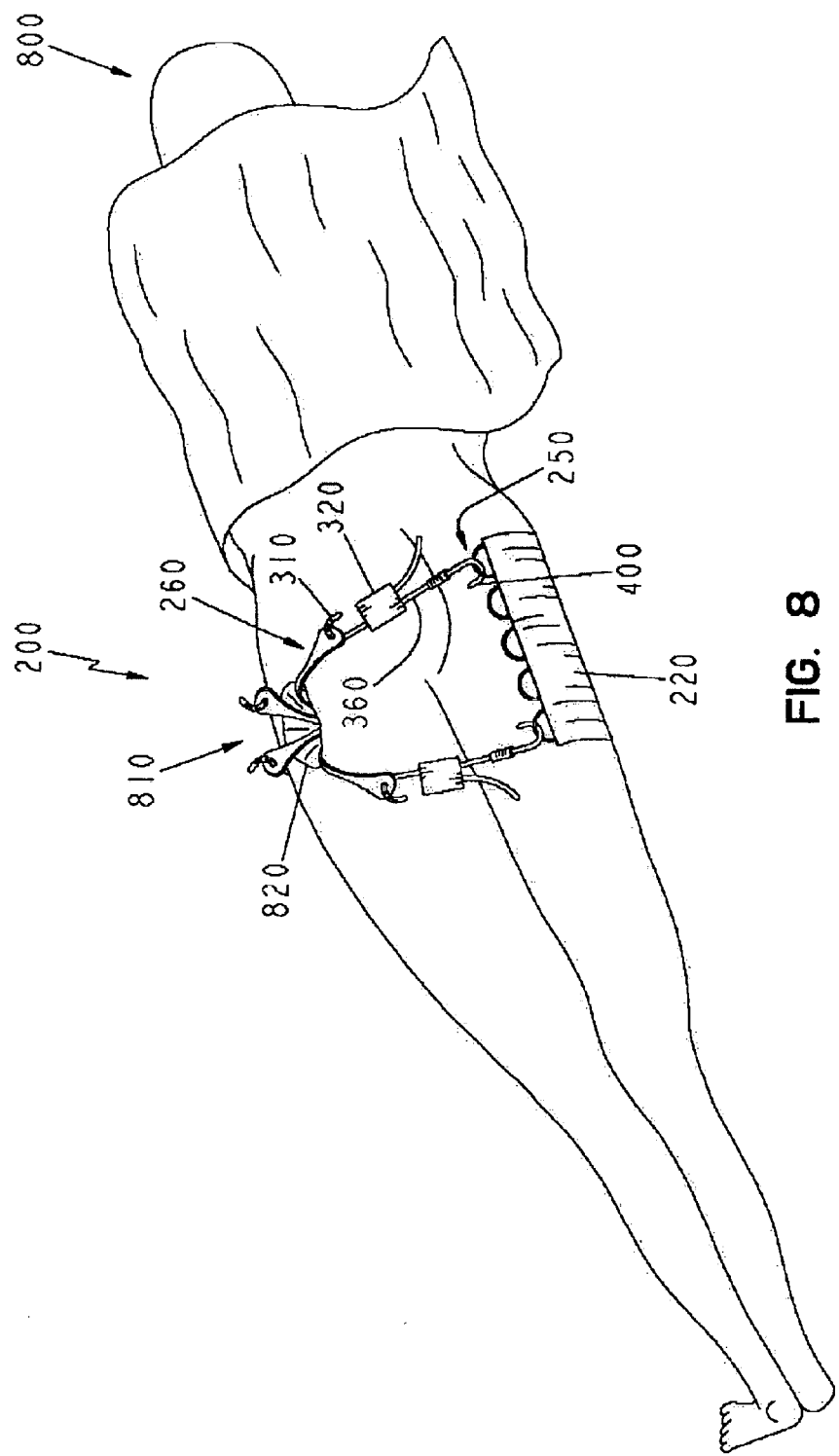
FIG. 8 shows an exemplary operational scenario for the exemplary surgical retractor system of FIG. 2.

FIG. 8 shows an exemplary operational scenario for exemplary surgical retractor system 200 of FIG. 2. In operation of system 200, fastener 310 is disengaged from retractor 260, and fastener 400 is disengaged from loops. Base 220 is spread out, and a patient 800 is placed on surface 230 (see FIG. 2) of base 220. In a known manner, a cavity 810 with a rim 820 is made or located in patient 800. Blade portion 270 (see FIG. 2) of retractor 260 is suitably positioned along rim 820 and fastener 400 is engaged with a suitable one of loops 250. With band 360 relaxed, catch 320 is positioned along band 360 such that band 360 must be suitably stretched (and thus, suitably tensioned) for re-engagement of fastener 310 with retractor 260, so as to apply an expansion force to cavity 810. Fastener 310 is then indeed re-engaged with base portion 280 of retractor 260 via aperture 290 (see FIG. 2), thereby stretching (and tensioning) band 360. Friction between band 360 and channel 330 (see FIG. 4) of catch 320 maintains the position of catch 320 and, in turn, maintains tension in band 360. Thus, system 200 expands cavity 810. Furthermore, FIG. 8 also shows that one or more additional retractors (configured like retractor 260; see FIG. 2) with one or more respective additional couplings (configured like coupling 300; see FIG. 2, FIG. 3, and FIG. 4) may be engaged with other of loops 250 or loops 240 for additional expansion of cavity 810 as desired. Exemplary system 500, exemplary system 600, and exemplary system 700 are operated in a like manner.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. An apparatus, comprising:
   a substantially pliable sheet-like member including a first perimeter side, further including a plurality of first attachment sites spaced along the first perimeter side and defining a plurality of apertures, further including a second perimeter side opposing the first perimeter side, and further including a plurality of second attachment sites spaced along the second perimeter side;

a first surgical retractor defining an aperture;

a first substantially elastic coupling extending between one of the first attachment sites and the first surgical retractor, the first coupling including an elastic member including a first portion and a second portion, the first coupling further including a catch member engaged with the first portion of the elastic member, the first coupling further including a first fastener extending from the catch member through the aperture defined by the first retractor, and the first coupling further including a second fastener extending from the second portion of the elastic member through at least one of the apertures defined by plurality of first attachment sites;

a second surgical retractor; and a second substantially elastic coupling extending between one of the second attachment sites and the second surgical retractor;

wherein the plurality of first attachment sites and the opposing plurality of second attachment sites facilitate varying a direction of a respective pulling force applied by each surgical retractor.

2. The apparatus of claim 1, wherein the plurality of apertures includes a row of loops.

3. The apparatus of claim 1, wherein the second fastener includes a hook.

4. An apparatus, comprising:

a substantially pliable sheet-like member including a first perimeter side, further including a plurality of first attachment sites spaced along the first perimeter side, further including a second perimeter side opposing the first perimeter side, and further including a plurality of second attachment sites spaced along the second perimeter side;

a first surgical retractor defining an aperture;

a first substantially elastic coupling extending between one of the first attachment sites and the first surgical retractor, the first coupling including an elastic member including a first portion and a second portion, the first coupling further including a catch member engaged with the first portion of the elastic member, the first coupling further including a first fastener extending from the catch member through the aperture defined by the first retractor;

a second surgical retractor; and a second substantially elastic coupling extending between one of the second attachment sites and the second surgical retractor;

wherein the plurality of first attachment sites defines an oblong aperture, the first coupling further includes a second fastener extending through the oblong aperture, and the plurality of first attachment sites and the opposing plurality of second attachment sites facilitate varying a direction of a respective pulling force applied by each surgical retractor.

5. The apparatus of claim 4, wherein the second fastener includes a hook.

6. An apparatus, comprising:

a substantially pliable sheet-like member including a first perimeter side, further including a plurality of first attachment sites spaced along the first perimeter side, further including a second perimeter side opposing the first perimeter side, and further including a plurality of second attachment sites spaced along the second perimeter side;

a first surgical retractor defining an aperture;

a first substantially elastic coupling extending between one of the first attachment sites and the first surgical retractor, the first coupling including an elastic member including a first portion and a second portion, the first coupling further including a catch member engaged with the first portion of the elastic member, the first coupling further including a first fastener extending from the catch member through the aperture defined by the first retractor; and the first coupling further including a pincer that grasps the sheet-like member;

a second surgical retractor; and a second substantially elastic coupling extending between one of the second attachment sites and the second surgical retractor;

wherein the plurality of first attachment sites and the opposing plurality of second attachment sites facilitate varying a direction of a respective pulling force applied by each surgical retractor.

7. An apparatus, comprising:

a substantially pliable sheet-like member including a first perimeter side, further including a plurality of first attachment sites spaced along the first perimeter side, further including a second perimeter side opposing the first perimeter side, and further including a plurality of second attachment sites spaced along the second perimeter side;

a first surgical retractor defining an aperture;

a first substantially elastic coupling extending between one of the first attachment sites and the first surgical retractor, the first coupling including an elastic member including a first portion and a second portion, the first coupling further including a catch member engaged with the first portion of the elastic member, the first coupling further including a first hook extending from the catch member through the aperture defined by the first retractor;

a second surgical retractor; and a second substantially elastic coupling extending between one of the second attachment sites and the second surgical retractor;

wherein the catch member defines a channel having a generally U-shaped cross-section, the first portion of the elastic member is positioned in the channel, the plurality of first attachment sites includes a row of loops, the first coupling further includes a second hook extending from the second portion of the elastic member through at least one of the loops, and the plurality of first attachment sites and the opposing plurality of second attachment sites facilitate varying a direction of a respective pulling force applied by each surgical retractor.

8. A method for expanding a surgical cavity in a patient having a body and a head, the body including a chest, an abdomen, and an upper thigh, the method comprising the steps of:

positioning the body of the patient on a substantially pliable sheet-like member;

positioning a surgical retractor in the cavity;

extending a substantially elastic coupling between the sheet-like member and the retractor; and tensioning the coupling.

9. The method of claim 8, wherein the step of positioning the body includes positioning the upper thigh on the substantially pliable sheet-like member.

10. The method of claim 8, wherein the step of positioning the surgical retractor in the cavity includes positioning the surgical retractor in at least one of the chest and the abdomen.

* * * * *